US011934491B1

United States Patent
Gilinsky et al.

(10) Patent No.: US 11,934,491 B1
(45) Date of Patent: Mar. 19, 2024

(54) SYSTEMS AND METHODS FOR IMAGE CLASSIFICATION AND STREAM OF IMAGES SEGMENTATION

(71) Applicant: Given Imaging LTD, Yoqneam (IL)

(72) Inventors: Alexandra Gilinsky, Haifa (IL); Avishai Adler, Haifa (IL); Eshel Hason, Yoqneam Illit (IL)

(73) Assignee: GIVEN IMAGING LTD., Yoqneam (IL)

( * ) Notice: Subject to any disclaimer, the term of this patent is extended or adjusted under 35 U.S.C. 154(b) by 512 days.

(21) Appl. No.: 17/244,988

(22) Filed: Apr. 30, 2021

Related U.S. Application Data

(60) Provisional application No. 63/018,878, filed on May 1, 2020.

(51) Int. Cl.
*G06F 18/2415* (2023.01)
*A61B 1/00* (2006.01)
*G06N 20/00* (2019.01)
*G06T 7/00* (2017.01)

(52) U.S. Cl.
CPC .... *G06F 18/2415* (2023.01); *A61B 1/000096* (2022.02); *G06N 20/00* (2019.01); *G06T 7/0012* (2013.01); *G06T 2207/10068* (2013.01); *G06T 2207/30028* (2013.01); *G06T 2207/30092* (2013.01)

(58) Field of Classification Search
CPC .......... G06F 18/2415; A61B 1/000096; G06N 20/00; G06T 7/0012; G06T 2207/10068; G06T 2207/30028; G06T 2207/30092
USPC .......................................................... 382/128
See application file for complete search history.

(56) References Cited

U.S. PATENT DOCUMENTS

| | | | |
|---|---|---|---|
| 2007/0232851 A1* | 10/2007 | Fujimori | A61B 1/041 600/109 |
| 2010/0130818 A1* | 5/2010 | Jung | A61B 1/00036 600/109 |
| 2019/0125173 A1 | 5/2019 | Lee et al. | |
| 2019/0175248 A1* | 6/2019 | Neal | A61B 18/1206 |
| 2021/0272317 A1* | 9/2021 | Patel | G06F 18/2413 |
| 2021/0358121 A1* | 11/2021 | Bangia | G06F 18/21 |

* cited by examiner

*Primary Examiner* — Juan A Torres
(74) *Attorney, Agent, or Firm* — Carter, DeLuca & Farrell LLP

(57) ABSTRACT

A method for image classification includes accessing a plurality of images of at least a portion of a gastrointestinal tract (GIT) captured by a capsule endoscopy device and for each image of the plurality of images: providing a classification score for each segment of a plurality of consecutive segments of the GIT by a deep learning neural network, and providing a classification probability for each segment of the plurality of consecutive segments of the GIT based on the classification scores by a classical machine learning classifier. The method further includes determining a classification for each image to one segment of the plurality of consecutive segments of the GIT based on processing a signal corresponding to the classification probabilities of the plurality of images.

22 Claims, 12 Drawing Sheets

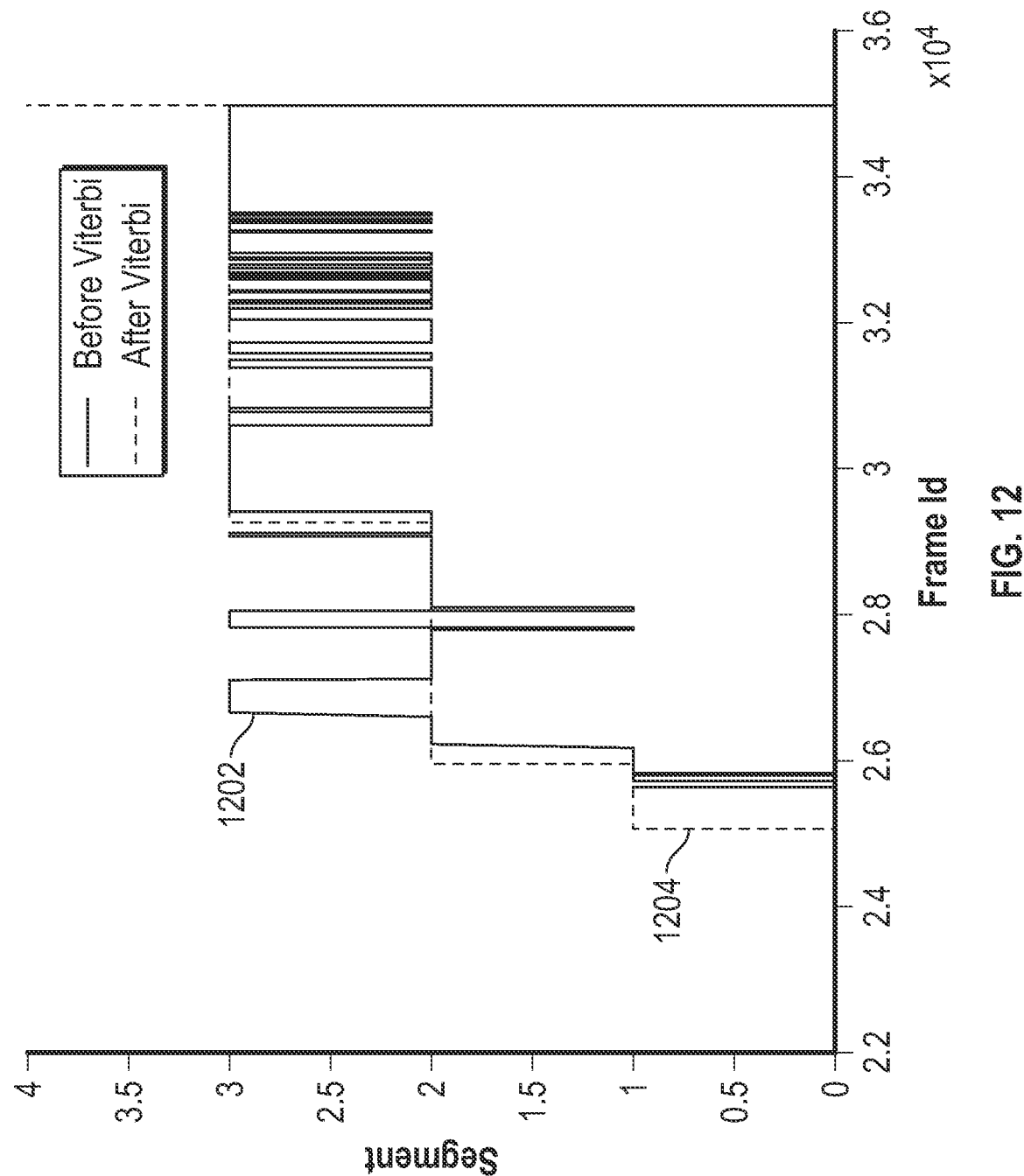

SYSTEMS AND METHODS FOR IMAGE CLASSIFICATION AND STREAM OF IMAGES SEGMENTATION

CROSS-REFERENCE TO RELATED APPLICATIONS

The present application claims the benefit of and priority to U.S. Provisional Application No. 63/018,878, filed May 1, 2020, which is hereby incorporated by reference herein in its entirety.

FIELD

The disclosure relates to image analysis methods and systems and, more particularly, to systems and methods for analyzing a stream of images using image classification and performing segmentation based on a change of image scenery.

BACKGROUND

Capsule endoscopy (CE) allows examining the entire gastrointestinal tract (GIT) endoscopically. There are capsule endoscopy systems and methods that are aimed at examining a specific portion of the GIT, such as the small bowel (SB) or the colon. CE is a non-invasive procedure that does not require the patient to be admitted to a hospital, and the patient can continue most daily activities while the capsule is in his body.

On a typical CE procedure, the patient is referred to a procedure by a physician. The patient then arrives at a medical facility (e.g., a clinic or a hospital), to perform the procedure. The capsule, which is about the size of a multivitamin, is swallowed by the patient under the supervision of a health professional (e.g., a nurse or a physician) at the medical facility and the patient is provided with a wearable device, e.g., a sensor belt and a recorder placed in a pouch and strap to be placed around the patient's shoulder. The wearable device typically includes a storage device. The patient may be given guidance and/or instructions and then released to his daily activities.

The capsule captures images as it travels naturally through the GIT. Images and additional data (e.g., metadata) are then transmitted to the recorder that is worn by the patient. The capsule is typically disposable and passes naturally with a bowel movement. The procedure data (e.g., the captured images or a portion of them and additional metadata) is stored on the storage device of the wearable device.

The wearable device is typically returned by the patient to the medical facility with the procedure data stored thereon. The procedure data is then downloaded to a computing device typically located at the medical facility, which has an engine software stored thereon. The received procedure data is then processed by the engine to a compiled study (or "study"). Typically, a study includes thousands of images (around 6,000 to 9,000). Typically, the number of images to be processed is of the order of tens of thousands and about 90,000 on average.

A reader (which may be the procedure supervising physician, a dedicated physician, or the referring physician) may access the study via a reader application. The reader then reviews the study, evaluates the procedure, and provides his input via the reader application. Since the reader needs to review thousands of images, the reading time of a study may usually take between half an hour to an hour on average, and the reading task may be tiresome. A report is then generated by the reader application based on the compiled study and the reader's input. On average, it would take an hour to review a study and generate a report. The report may include, for example, images of interest, e.g., images which are identified as including pathologies, selected by the reader; evaluation or diagnosis of the patient's medical condition based on the procedure's data (i.e., the study) and/or recommendations for follow up and/or treatment provided by the reader. The report may then be forwarded to the referring physician. The referring physician may decide on a required follow up or treatment based on the report.

SUMMARY

The present disclosure relates to systems and methods for analyzing a stream of images of a gastrointestinal tract (GIT). More particularly, the present disclosure relates to systems and methods for analyzing a stream of images using image classification and performing segmentation. As used herein, the term "segmentation" may refer to the identification of one or more transition points in a stream of images. Even though examples are shown and described with respect to images captured in vivo by a capsule endoscopy device, the disclosed technology can be applied to images captured by other devices or mechanisms, including anatomical images captured by Mill, for example.

As used herein, the term "distal" refers to the portion that is being described which is further from a user, while the term "proximal" refers to the portion that is being described which is closer to a user. Further, to the extent consistent, any or all of the aspects detailed herein may be used in conjunction with any or all of the other aspects detailed herein.

Provided in accordance with aspects of the disclosure is a system for image classification. The system includes a processor and memory. The memory includes instructions stored thereon which, when executed by the at least one processor, cause the system to: access a plurality of images of at least a portion of a gastrointestinal tract (GIT) captured by a capsule endoscopy device and for each image of the plurality of images: provide a classification score for each segment of a plurality of consecutive segments of the GIT by at least one deep learning neural network, and provide a classification probability for each segment of the plurality of consecutive segments of the GIT based on the classification scores by a classical machine learning classifier. The instructions when executed further cause the system to determine a classification for each image to one segment of the plurality of consecutive segments of the GIT based on processing a signal corresponding to the classification probabilities of the plurality of images.

In an aspect of the present disclosure, in providing the classification probability, the instructions, when executed by the processor, may cause the system to, for each image of the plurality of images: access a score of an anatomical landmark detection for the image, and provide the classification probability based on the score of the anatomical landmark detection.

In another aspect of the present disclosure, the anatomical landmark is the ileocecal valve.

In another aspect of the present disclosure, the instructions, when executed by the at least one processor, may cause the system to display, on a display, an indication of a location of the image corresponding to a segment of the GIT based on the determined classification.

In another aspect of the present disclosure, the classical machine learning classifier may include a linear logistic regression classifier.

In still another aspect of the present disclosure, the instructions, when executed by the processor, may further cause the system to receive an indication that one image of the plurality of images includes an exit image.

In yet another aspect of the present disclosure, in providing the classification score, the instructions, when executed by the processor, may cause the system to, for each image of the plurality of images: in a case where the indication is received, include as input to the classical machine learning classifier at least one cue which is based on the indication of the exit image.

In an aspect of the present disclosure, the cue may include at least one of: a time percentage indicating a time that the capsule endoscopy device captured the image over a time duration that the capsule endoscopy device was within a GIT portion of interest, and/or a progress percent indicating a displacement of the capsule up until each image and relative to a whole GIT portion to be imaged.

In an aspect of the present disclosure, processing the signal may include a Modified A Posteriori Probability (MAPP) decoding and/or a Viterbi decoding based on a Hidden Markov Model of transitions between the consecutive segments of the GIT.

In another aspect of the present disclosure, the Hidden Markov Model may include a predetermined number of states that is a multiple of a number of the consecutive segments of the GIT.

In still yet another aspect of the present disclosure, in processing the signal, the instructions, when executed by the processor, may further cause the system to: apply a non-zero initial state probability for one segment of the plurality of consecutive segments of the GIT; and apply a zero initial state probability for at least one other segment of the plurality of consecutive segments.

Provided in accordance with aspects of the disclosure is a method for image classification. The method includes accessing a plurality of images of a portion of a gastrointestinal tract (GIT) captured by a capsule endoscopy device and for each image of the plurality of images: providing a classification score for each segment of a plurality of consecutive segments of the GIT by at least one deep learning neural network, and provide a classification probability for each segment of the plurality of consecutive segments of the GIT based on the classification scores by a classical machine learning classifier. The method further includes determining a classification for each image to one segment of the plurality of consecutive segments of the GIT based on processing a signal corresponding to the classification probabilities of the plurality of images.

In an aspect of the present disclosure, providing the classification probability may include, for each image of the plurality of images: accessing a score of an anatomical landmark detection for the image and providing the classification probability based on the score of the anatomical landmark detection.

In another aspect of the present disclosure, the method may further include displaying, on a display, an indication of a location of the image corresponding to a segment of the GIT based on the determined classification.

In another aspect of the present disclosure, the classical machine learning classifier may include a linear logistic regression classifier.

In still another aspect of the present disclosure, the method may further include receiving an indication that at least one image of the plurality of images includes an exit image.

In another aspect, providing the classification score probability includes, for each image of the plurality of images: in a case where the indication is received, including as input to the classical machine learning classifier at least one cue which is based on the indication of the exit image.

In an aspect of the present disclosure, processing the signal may include at least one of MAPP decoding or Viterbi decoding based on a Hidden Markov Model of transitions between the consecutive segments of the GIT.

Provided in accordance with aspects of the disclosure is a system for image classification. The system includes a processor and a memory. The memory includes instructions stored thereon which, when executed by the at least one processor, cause the system to: access a time series of images of at least a portion of a gastrointestinal tract (GIT) captured by a capsule endoscopy device and for each image of the time series of images; classify the image to one segment of a plurality of consecutive segments of the GIT based on classification scores provided by at least one deep learning neural network; and perform error correction to revise the classification of at least one image of the images of the time series of images.

In another aspect of the present disclosure, performing error correction to revise at least one of the classifications, the instructions, when executed by the at least one processor, causes the system to display, on a display, an indication of a location of the image corresponding to a segment of the GIT based on the revised classification.

In another aspect of the present disclosure, performing error correction includes a MAPP decoding and/or a Viterbi decoding based on a Hidden Markov Model of transitions between the consecutive segments of the GIT.

In another aspect of the present disclosure, the at least portion of the GIT is the colon.

Further details and aspects of exemplary embodiments of the present disclosure are described in more detail below with reference to the appended figures.

BRIEF DESCRIPTION OF DRAWINGS

The above and other aspects and features of the disclosure will become more apparent in view of the following detailed description when taken in conjunction with the accompanying drawings wherein like reference numerals identify similar or identical elements.

FIGS. 11 and 12, are graphs illustrating classifications of the plurality of images over time after the various steps of the method FIG. 10 are shown in accordance with aspects of the present disclosure.

DETAILED DESCRIPTION

Figure 1:
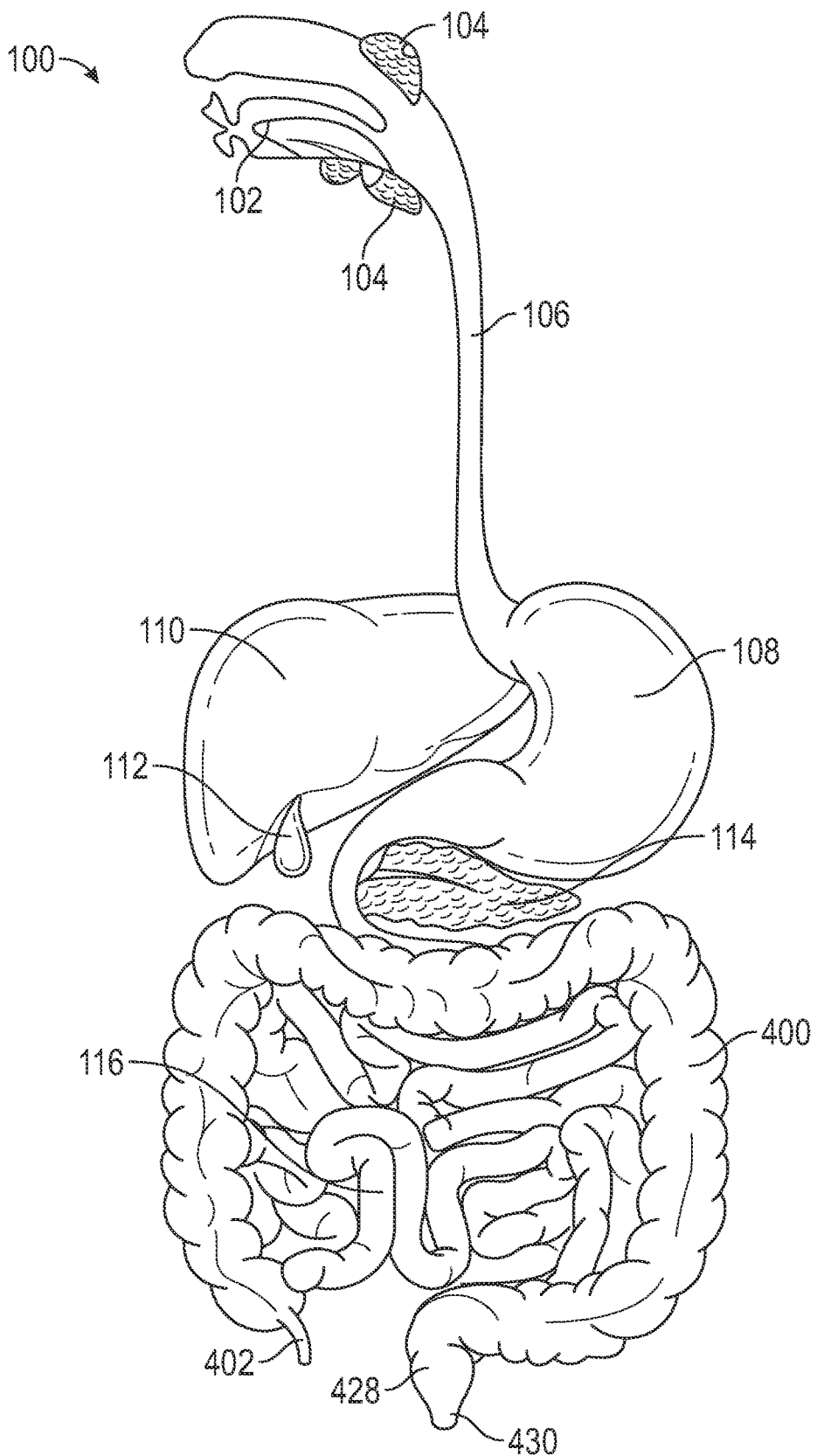
FIG. 1 is a diagram illustrating a gastrointestinal tract (GIT)

The disclosure relates to systems and methods for analyzing medical images and, more particularly, to systems and methods for segmenting a stream of images captured in vivo via a Capsule Endoscopy (CE) procedure. Even though the examples are shown and described with respect to images captured in vivo by a CE device, the disclosed technology can be applied to images captured by other devices, mechanisms or procedures, including colonoscopy and enteroscopy procedures and anatomical images captured by MRI, for example. The disclosed technology may be applied in an offline mode (e.g., to an image stream captured by CE procedure after the procedure is complete) or in an online mode (e.g., during a CE, colonoscopy or enteroscopy procedures to images which have been already captured), by applying, for example, the non-casual case, as will be detailed herein below.

In the following detailed description, specific details are set forth in order to provide a thorough understanding of the disclosure. However, it will be understood by those skilled in the art that the disclosure may be practiced without these specific details. In other instances, well-known methods, procedures, and components have not been described in detail so as not to obscure the present disclosure. Some features or elements described with respect to one system may be combined with features or elements described with respect to other systems. For the sake of clarity, discussion of same or similar features or elements may not be repeated.

Although the disclosure is not limited in this regard, discussions utilizing terms such as, for example, "processing," "computing," "calculating," "determining," "establishing," "analyzing," "checking," or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium that may store instructions to perform operations and/or processes. Although the disclosure is not limited in this regard, the terms "plurality" and "a plurality" as used herein may include, for example, "multiple" or "two or more." The terms "plurality" or "a plurality" may be used throughout the specification to describe two or more components, devices, elements, units, parameters, or the like. The term set, when used herein, may include one or more items. Unless explicitly stated, the methods described herein are not constrained to a particular order or sequence. Additionally, some of the described methods or elements thereof can occur or be performed simultaneously, at the same point in time, or concurrently.

The term "location" and its derivatives, as referred to herein with respect to an image, may refer to the estimated location of the capsule along the GIT while capturing the image or to the estimated location of the portion of the GIT shown in the image along the GIT.

A type of CE procedure may be determined based on, inter alia, the portion of the GIT that is of interest and is to be imaged (e.g., the colon or the small bowel ("SB")), or based on the specific use (e.g., for checking the status of a GI disease, such as Crohn's disease, or for colon cancer screening).

The terms "surrounding" or "adjacent" as referred to herein with respect to images (e.g., images that surround another image(s), or that are adjacent to other image(s)), may relate to spatial and/or temporal characteristics unless specifically indicated otherwise. For example, images that surround or are adjacent to other image(s) may be images that are estimated to be located near the other image(s) along the GIT and/or images that were captured near the capture time of another image, within a certain threshold, e.g., within one or two centimeters, or within one, five, or ten seconds.

The terms "GIT" and "a portion of the GIT" may each refer to or include the other, according to their context. Thus, the term "a portion of the GIT" may also refer to the entire GIT, and the term "GIT" may also refer only to a portion of the GIT.

The terms "image" and "frame" may each refer to or include the other and may be used interchangeably in the present disclosure to refer to a single capture by an imaging device. For convenience, the term "image" may be used more frequently in the present disclosure, but it will be understood that references to an image shall apply to a frame as well.

The term "classification score(s)" or "score(s)" may be used throughout the specification to indicate a value or a vector of values for a category or a set of categories applicable to an image/frame. In various implementations, the value or vector of values of a classification score or classification scores may be or may reflect probabilities. In various embodiments, a model may output classification scores which may be probabilities. In various embodiments, a model may output classification scores which may not be probabilities.

The term "classification probabilities" may be used to describe classification scores which are probabilities or to describe a transformation of classification scores which are not probabilities into values which reflect the probabilities that each category of the set of categories applies to the image/frame. It will be understood from context that various references to "probability" refer to and are a shorthand for a classification probability.

As used herein, the terms "segmentation" or "divide" may refer to the division of a stream of images into different portions or segments of images. According to some aspects, the segmentation or division of the stream of images may provide consecutive portions or segments. According to some aspects, each of the portions or segments of the stream of images may include images of a portion or a segment of the GIT, correspondingly. According to some aspects the segmentation or division may be based on identification of one or more transition points between different segments or portions of the GIT in the stream of images. According to some aspects, the stream of images may include consecutive images captured, for example, via a capsule device during a CE procedure while the capsule device traverses a portion of the GIT.

Referring to FIG. 1, an illustration of the GIT 100 is shown. The GIT 100 is an organ system within humans and other animals. The GIT 100 generally includes a mouth 102 for taking in sustenance, salivary glands 104 for producing saliva, an esophagus 106 through which food passes aided by contractions, a stomach 108 to secret enzymes and stomach acid to aid in digesting food, a liver 110, a gall bladder 112, a pancreas 114, a small intestine 116 (e.g., SB) for the absorption of nutrients, and a colon 400 (e.g., large intestine) for storing water and waste material as feces prior to defecation. The colon 400 generally includes an appendix 402, a rectum 428, and an anus 430. Food taken in through the mouth is digested by the GIT to take in nutrients, and the remaining waste is expelled as feces through the anus 430.

Studies of different portions of the GIT 100 e.g., SB 116, colon 400, esophagus 106, and/or stomach 108 may be presented via a suitable user interface. As used herein, the term "study" refers to and includes at least a set of images selected from the images captured by a CE imaging device (e.g., 212, FIG. 2) during a single CE procedure performed with respect to a specific patient and at a specific time, and can optionally include information other than images as well. The type of procedure performed may determine which portion of the GIT 100 is the portion of interest. Examples of types of procedures performed include, without limitation, an esophagus procedure, an SB procedure, a colon procedure, an SB and colon procedure, a procedure aimed to specifically exhibit or check the SB, a procedure aimed to specifically exhibit or check the colon, a procedure aimed to specifically exhibit or check the colon and the SB, or a procedure to exhibit or check the entire GIT: esophagus, stomach, SB and colon.

Figure 2:
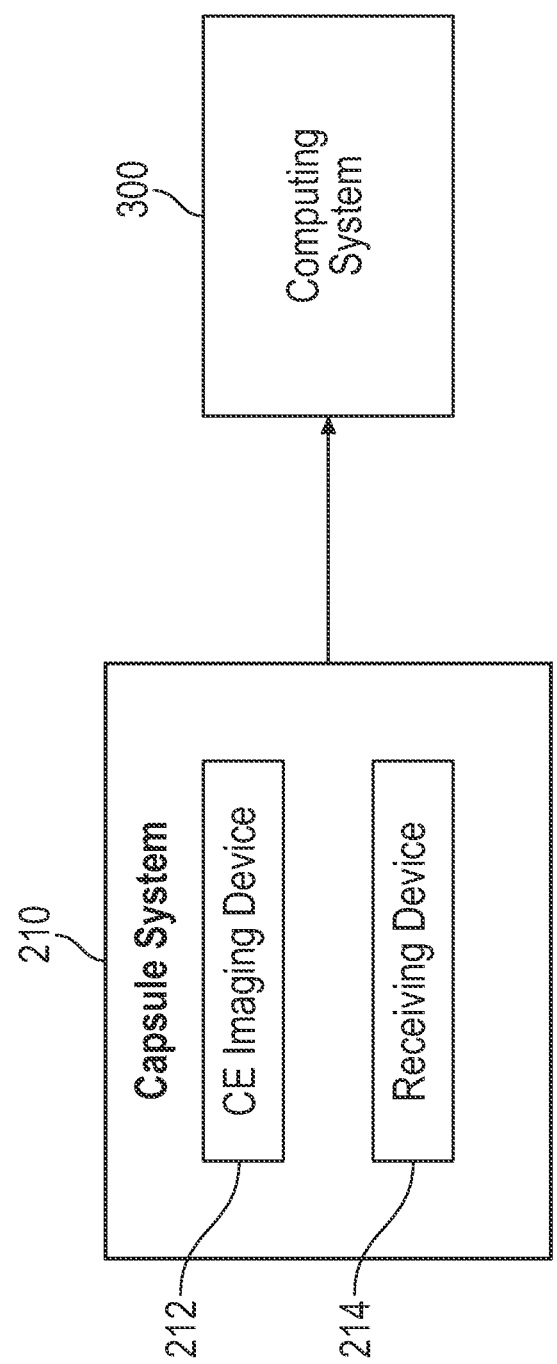
FIG. 2 is a high-level block diagram of an exemplary system for analyzing medical images captured in vivo via a Capsule Endoscopy (CE) procedure in accordance with aspects of the disclosure.

FIG. 2 shows a block diagram of a system for analyzing medical images captured in vivo via a CE procedure. The system generally includes a capsule system 210 configured to capture images of the GIT, and a computing system 300 (e.g., local system and/or cloud system or platform) configured to process the captured images.

The capsule system 210 may include a swallowable CE imaging device 212 (e.g., a capsule) configured to capture images of the GIT as the CE imaging device 212 travels through the GIT. The images may be stored on the CE imaging device 212 and/or transmitted to a receiving device 214, typically including an antenna. In some capsule systems 210, the receiving device 214 may be located on the patient who swallowed the CE imaging device 212 and may, for example, take the form of a belt worn by the patient or a patch secured to the patient.

The capsule system 210 may be communicatively coupled with the computing system 300 and can communicate captured images to the computing system 300. The computing system 300 may process the received images using image processing technologies, machine learning technologies, and/or signal processing technologies, among other technologies. The computing system 300 can include local computing devices that are local to the patient and/or the patient's treatment facility, a cloud computing platform that is provided by cloud services, or a combination of local computing devices and a cloud computing platform.

In the case where the computing system 300 includes a cloud computing platform, the images captured by the capsule system 210 may be transmitted online or offline to the cloud computing platform. In various embodiments, the images can be transmitted via the receiving device 214 worn or carried by the patient. In various embodiments, the images can be transmitted via the patient's smartphone or via any other device connected to the Internet and which may be coupled with the CE imaging device 212 or the receiving device 214.

Figure 3:
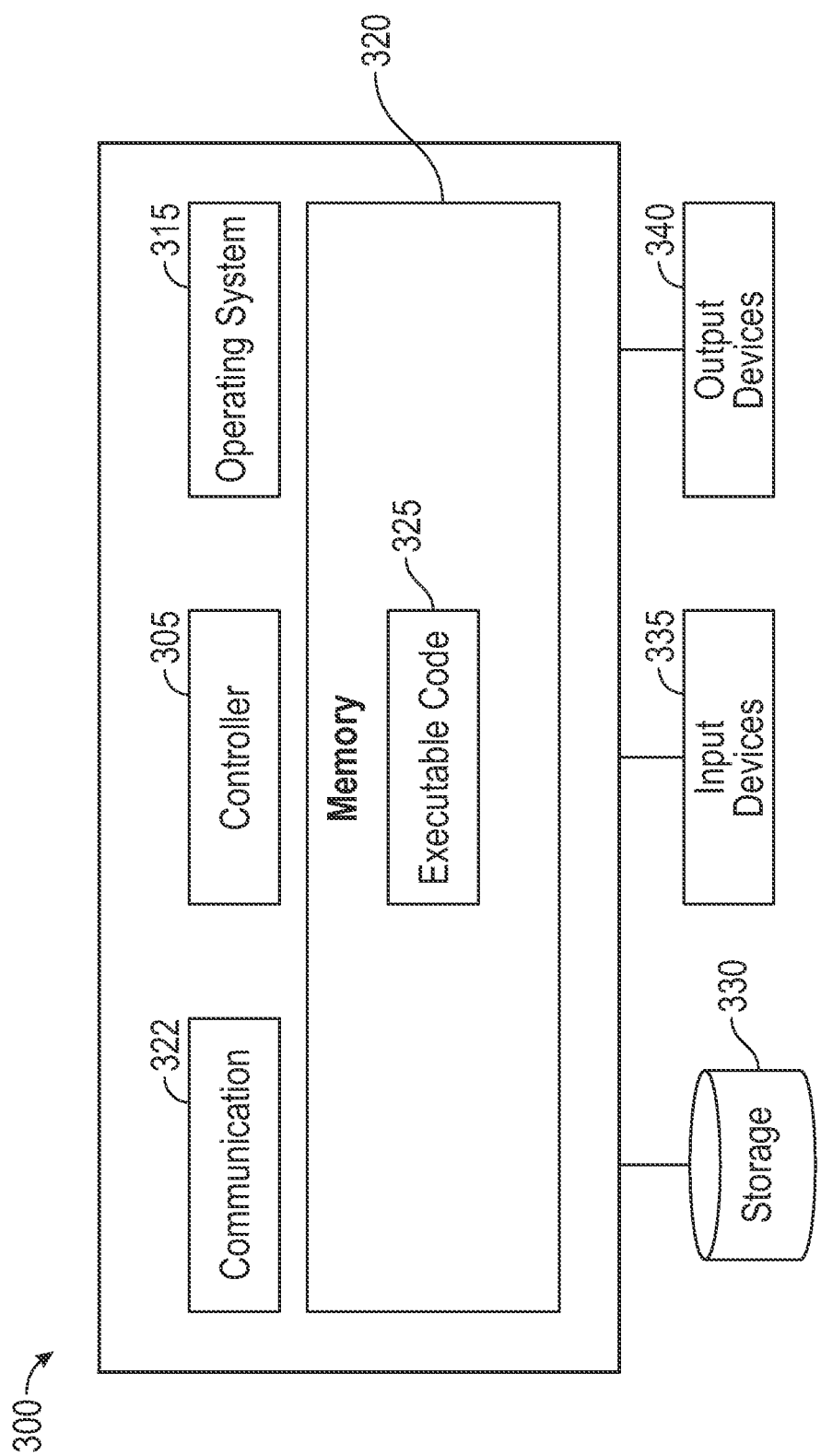
FIG. 3 is a high-level block diagram of an exemplary computing device which may be used with the systems of the disclosure.

FIG. 3 shows a high-level block diagram of an exemplary computing system 300 that may be used with image analyzing systems of the present disclosure. Computing system 300 may include a processor or controller 305 that may be or include, for example, one or more central processing unit processor(s) (CPU), one or more Graphics Processing Unit(s) (GPU or GPGPU), a chip or any suitable computing or computational device, an operating system 315, a memory 320, a storage 330, input devices 335 and output devices 340. Modules or equipment for collecting or receiving (e.g., a receiver worn on a patient) or displaying or selecting for display (e.g., a workstation) medical images collected by the CE imaging device 212 (FIG. 2) may be or include, or may be executed by, the computing system 300 shown in FIG. 3. A communication component 322 of the computing system 300 may allow communications with remote or external devices, e.g., via the Internet or another network, via radio, or via a suitable network protocol such as File Transfer Protocol (FTP), etc.

The computing system 300 includes an operating system 315 that may be or may include any code segment designed and/or configured to perform tasks involving coordination, scheduling, arbitration, supervising, controlling or otherwise managing operation of computing system 300, for example, scheduling execution of programs. Memory 320 may be or may include, for example, a Random Access Memory (RAM), a read-only memory (ROM), a Dynamic RAM (DRAM), a Synchronous DRAM (SD-RAM), a double data rate (DDR) memory chip, a Flash memory, a volatile memory, a non-volatile memory, a cache memory, a buffer, a short term memory unit, a long term memory unit, or other suitable memory units or storage units. Memory 320 may be or may include a plurality of possibly different memory units. Memory 320 may store, for example, instructions to carry out a method (e.g., executable code 325), and/or data such as user responses, interruptions, etc.

Executable code 325 may be any executable code, e.g., an application, a program, a process, task or script. Executable code 325 may be executed by controller 305, possibly under the control of operating system 315. For example, execution of executable code 325 may cause the display or selection for display of medical images as described herein. In some systems, more than one computing system 300 or components of computing system 300 may be used for multiple functions described herein. For the various modules and functions described herein, one or more computing systems 300 or components of computing system 300 may be used. Devices that include components similar or different to those included in the computing system 300 may be used and may be connected to a network and used as a system. One or more processor(s) 305 may be configured to carry out methods of the present disclosure by for example executing software or code. Storage 330 may be or may include, for example, a hard disk drive, a floppy disk drive, a Compact Disk (CD) drive, a CD-Recordable (CD-R) drive, a universal serial bus (USB) device or other suitable removable and/or fixed storage unit. Data such as instructions, code, medical images, image streams, metadata, etc. may be stored in storage 330 and may be loaded from storage 330 into memory 320 where it may be processed by controller 305. In some embodiments, some of the components shown in FIG. 3 may be omitted, such as input devices 335 or and/or output devices 340.

Input devices 335 may include, for example, a mouse, a keyboard, a touch screen or pad, or any suitable input device. It will be recognized that any suitable number of input devices may be operatively coupled to computing system 300. Output devices 340 may include one or more monitors, screens, displays, speakers and/or any other suitable output devices. It will be recognized that any suitable number of output devices may be operatively coupled to computing system 300 as shown by block 340. Any applicable input/output (I/O) devices may be operatively coupled to computing system 300, for example, a wired or wireless network interface card (NIC), a modem, printer or facsimile machine, a universal serial bus (USB) device or external hard drive may be included in input devices 335 and/or output devices 340.

Multiple computer systems 300 including some or all of the components shown in FIG. 3 may be used with the described systems and methods. For example, a CE imaging device 212, a receiver, a cloud-based system, and/or a workstation or portable computing device for displaying images may include some or all of the components of the computer system of FIG. 3. A cloud platform (e.g., a remote server) including components such as computing system 300 of FIG. 3 may receive procedure data such as images and metadata, processes and generate a study, and may also display the generated study for the doctor's review (e.g., on a web browser executed on a workstation or portable computer). An "on-premise" option may use a workstation or local server of a medical facility to store, process and display images and/or a study.

Figure 4:
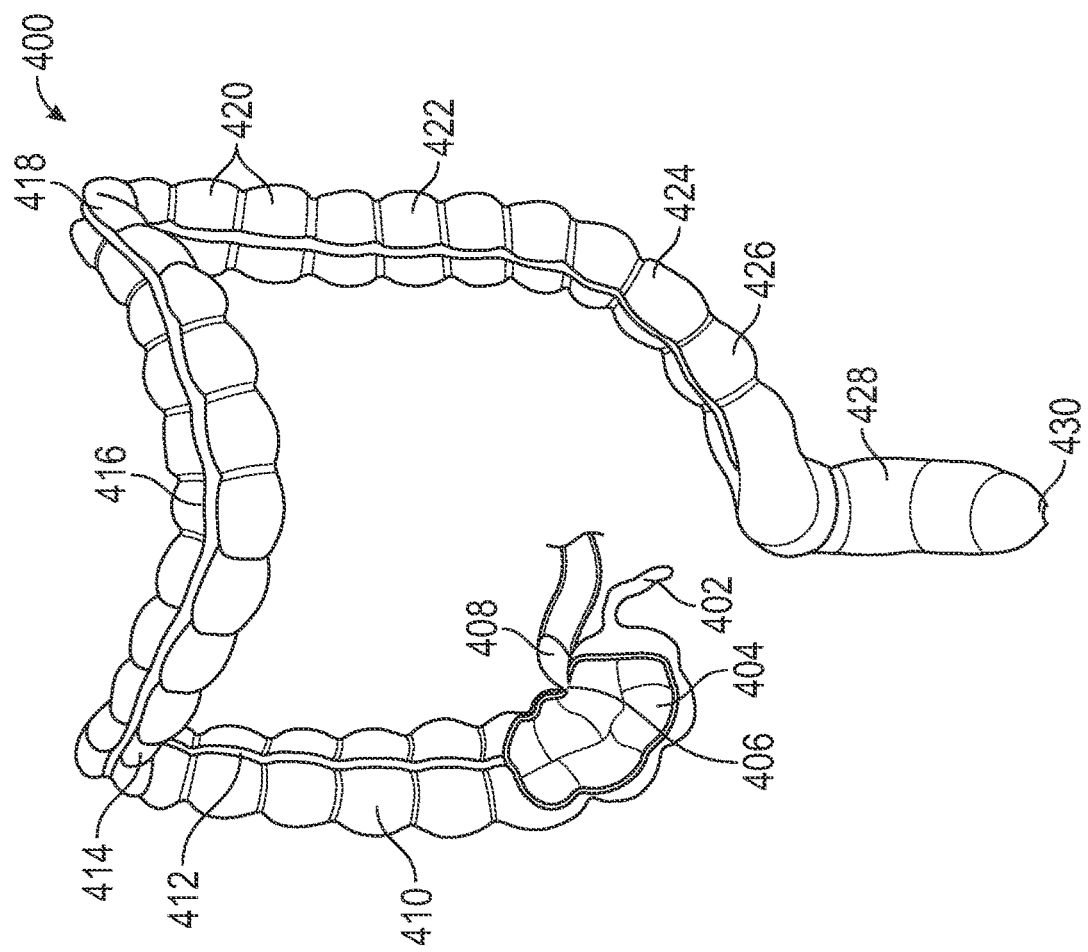
FIG. 4 is a diagram illustrating a large intestine.
Figure 4:
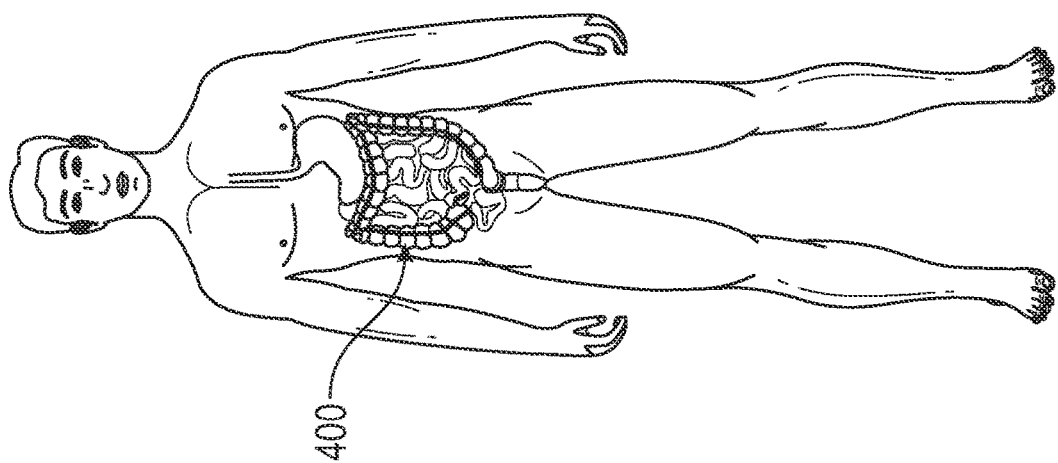

According to some aspects of the present disclosure, a user (e.g., a physician), may build his or her understanding of a case by reviewing a study, which includes a display of images (e.g., captured by the CE imaging device 212) that were selected, e.g., automatically, as images that may be of interest. With reference to FIG. 4, an illustration of the colon 400 is shown. The colon 400 absorbs water, and any remaining waste material is stored as feces before being removed by defecation. The colon 400 may be divided, for example, into five anatomical segments: cecum 404, right or ascending colon 410, transverse colon 416, left or descending colon 422 (e.g., left colon-sigmoid 424), and rectum 428.

A terminal ileum 408 is the final section of the SB and leads to the cecum 404 and is separated from the cecum 404 by a muscle valve called the ileocecal valve (ICV) 406. The ICV 406 also connects the terminal ilium 408 to the ascending colon 410. The cecum 404 is the first section of the colon 400. The cecum 404 includes the appendix 402. The next portion of the colon 400 is the ascending colon 410. The ascending colon 410 runs upwards through the abdominal cavity toward the transverse colon 416.

The transverse colon 416 is the part of the colon 400 from the hepatic flexure, also known as the right colic flexure 414, (the turn of the colon 400 by the liver) to the splenic flexure also known as the left colic flexure 418, (the turn of the colon 400 by the spleen). The transverse colon 416 hangs off the stomach, attached to it by a large fold of peritoneum called the greater omentum. On the posterior side, the transverse colon 416 is connected to the posterior abdominal wall by a mesentery known as the transverse mesocolon.

The descending colon 422 is the part of the colon 400 from the left colic flexure 418 to the beginning of the sigmoid colon 426. One function of the descending colon 422 in the digestive system is to store feces that will be emptied into the rectum. The descending colon 422 is also called the distal gut, as it is further along the gastrointestinal tract than the proximal gut. Gut flora is generally very dense in this region. The sigmoid colon 426 is the part of the colon 400 after the descending colon 422 and before the rectum 428. The name sigmoid means S-shaped. The walls of the sigmoid colon 426 are muscular, and contract to increase the pressure inside the colon 400, causing the stool to move into the rectum 428. The sigmoid colon 426 is supplied with blood from several branches (usually between 2 and 6) of the sigmoid arteries.

The rectum 428 is the last section of the colon 400. The rectum 428 holds the formed feces awaiting elimination via defecation.

The CE imaging device 212 (FIG. 2) may be used to image the interior of the colon 400. The entrance from the SB into the colon 400 happens through the ICV 406. Usually, after entering the colon 400 through the ICV 406, the CE imaging device 212 goes into the cecum 404. However, occasionally, the CE imaging device 212 misses the cecum 404 and goes straight into the ascending colon 410. The colon 400 may be wide enough to enable almost unrestricted CE imaging device 212 movement. The CE imaging device 212 may rotate and roll. The CE imaging device 212 may rest in one place for a long period of time, it may move very fast through the colon 400, or it may move back through a prior segment of the colon 400.

In general, the division of the GIT into anatomical segments may be performed, for example, based on the identification of the CE imaging device 212 passage between the different anatomical segments. Such identification may be performed, for example, based on machine learning techniques. It is contemplated that segmentation is not limited only to segmentation based on or according to the anatomical segments of the segmented portion. Segmentation according to the disclosed systems, methods and/or techniques may also be according to other criterions, e.g., according to sick and healthy segments of the portion of interest, and/or according to specific pathologies, and/or combinations of such. For example, diseases such as Crohn are characterized by diffused pathologies that spread on portions of the GIT in an almost "carpet" like manner.

Figure 5:
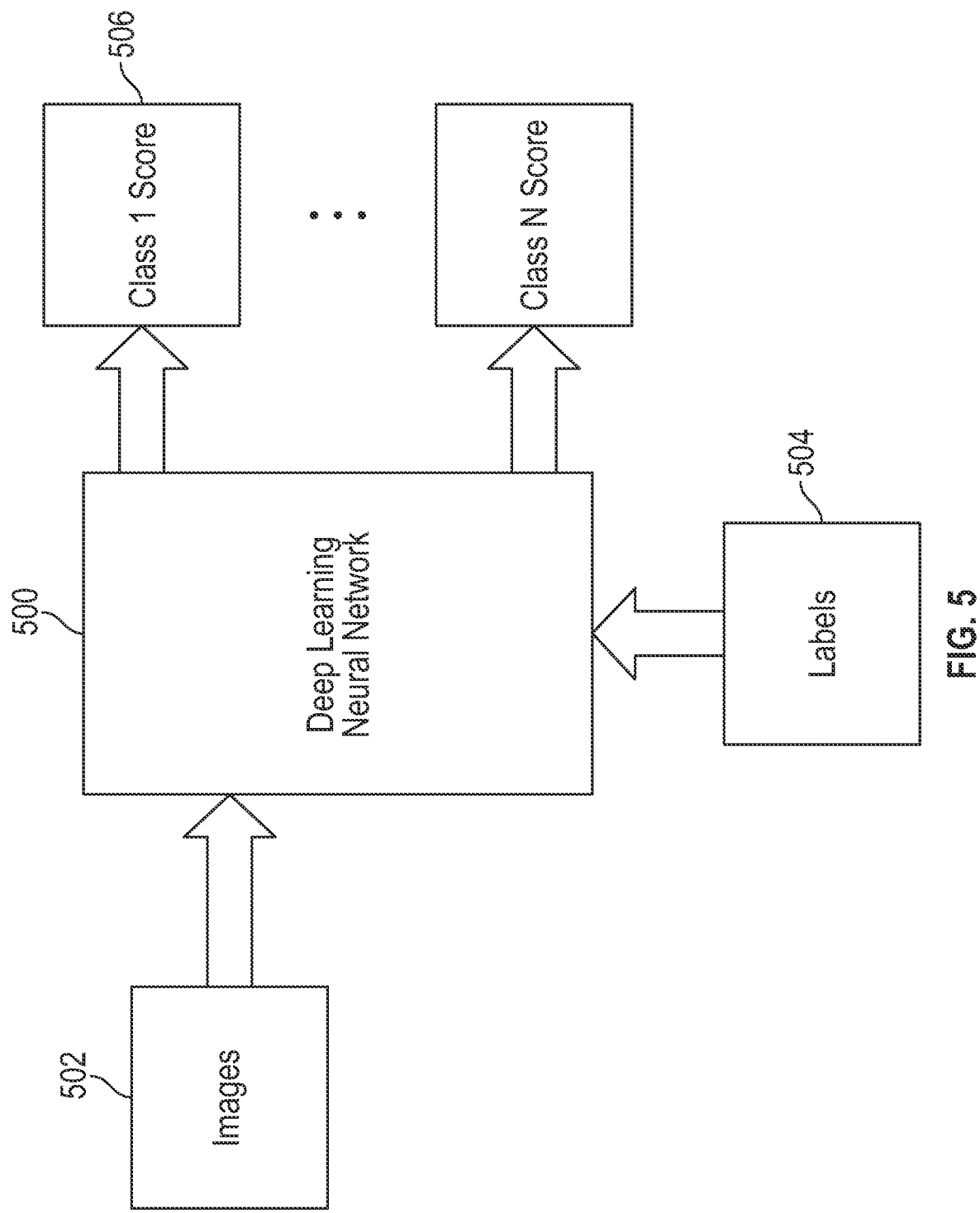
FIGS. 5 and 6 are diagrams of a deep learning neural network in accordance with aspects of the disclosure.
Figure 6:
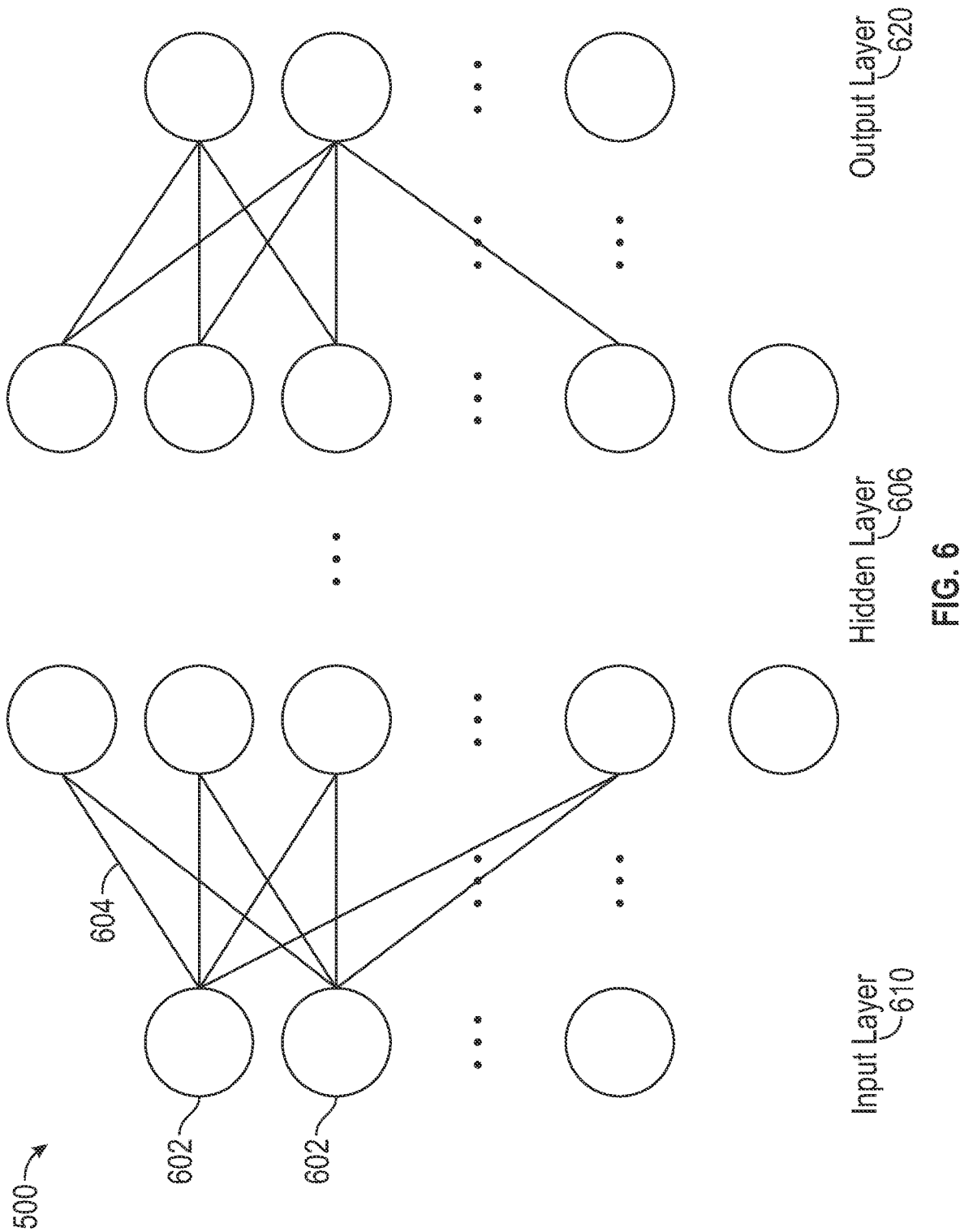

With reference to FIGS. 5 and 6 block diagrams for a deep learning neural network 500 for classifying images are shown in accordance with some aspects of the disclosure. In some systems, a deep learning neural network 500 may include, for example, a convolutional neural network (CNN) and/or a recurrent neural network. Generally, a deep learning neural network includes multiple hidden layers. As explained in more detail below, the deep learning neural network 500 may leverage one or more CNNs to classify one or more images, taken by the CE imaging device 212 (see FIG. 2), as a portion or a segment of the GIT. In various methods, the one or more CNNs may have a different amount of classification or classification categories from each other. For example, a first CNN may be a five-class CNN, and a second CNN may be a six-class CNN. The deep learning neural network 500 may be executed on the computer system 300 (FIG. 3). Persons skilled in the art will understand the deep learning neural network 500 and how to implement it.

In machine learning, a CNN is a class of artificial neural network (ANN), most commonly applied to analyzing visual imagery. The convolutional aspect of a CNN relates to applying matrix processing operations to localized portions of an image, and the results of those operations (which can involve dozens of different parallel and serial calculations) are sets of many features that are delivered to the next layer. A CNN typically includes convolution layers, activation function layers, and pooling (typically max pooling) layers to reduce dimensionality without losing too many features. Additional information may be included in the operations that generate these features. Providing unique information that yields features that give the neural networks information can be used to ultimately provide an aggregate way to differentiate between different data input to the neural networks.

Generally, a deep learning neural network 500 (e.g., a convolutional deep learning neural network) includes an input layer 610, a plurality of hidden layers 606, and an output layer 620. The input layer 610, the plurality of hidden layers 606, and the output layer 620 are all comprised of neurons 602 (e.g., nodes). The neurons 602 between the various layers are interconnected via weights 604. Each neuron 602 in the deep learning neural network 500 computes an output value by applying a specific function to the input values coming from the previous layer. The function that is applied to the input values is determined by a vector of weights 604 and a bias. Learning, in the deep learning neural network, progresses by making iterative adjustments to these biases and weights. The vector of weights 604 and the bias are called filters (e.g., kernels) and represent particular features of the input (e.g., a particular shape). The deep learning neural network 500 may output logits.

The deep learning neural network 500 may be trained based on labeling training images and/or objects in training images. For example, an image may be as a portion of the GIT (for example, the rectum or the cecum). In some methods in accordance with this disclosure, the training may include supervised learning. The training further may include augmenting the training images to include adding noise, changing colors, hiding portions of the training images, scaling of the training images, rotating the training images, and/or stretching the training images. Persons skilled in the art will understand training the deep learning neural network 500 and how to implement it.

In some methods in accordance with this disclosure, the deep learning neural network 500 may be used to classify images captured by the CE imaging device 212 (see FIG. 2). The classification of the images may include each image being classified as consecutive segments of the GIT. For example, the image classifications may include the cecum, the ascending colon, the transverse colon, the descending colon, and the rectum. Each of the images may include a classification score for each of the consecutive segments of the GIT. A classification score includes the outputs (e.g., logits) of the classical machine learning classifier 700 after applying a function such as a SoftMax to make the outputs represent probabilities.

Figure 7:
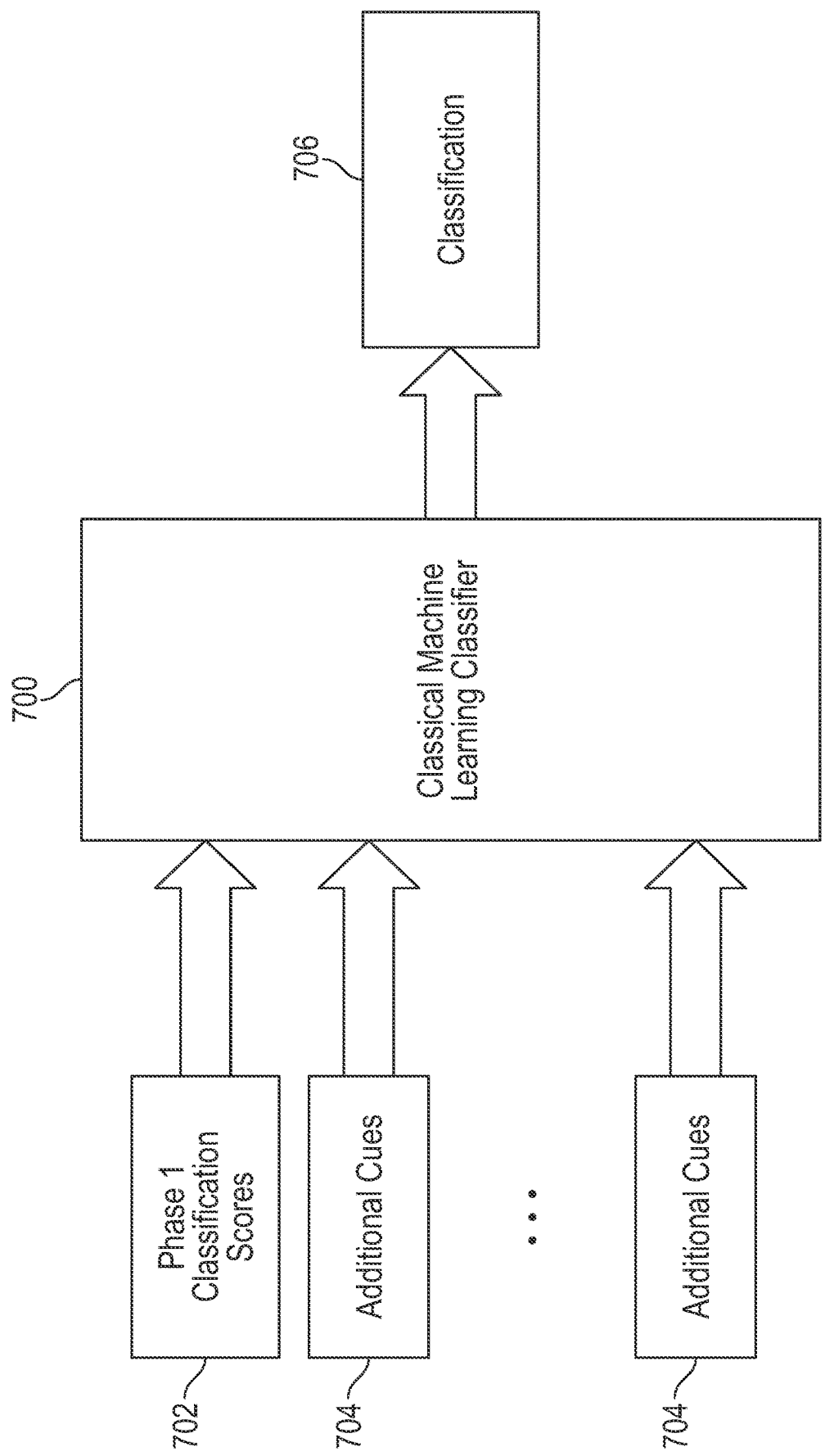
FIG. 7 is a block diagram of a classical machine learning classifier in accordance with aspects of the disclosure.

With reference to FIG. 7, a classical machine learning classifier 700 is shown in accordance with some aspects of the disclosure. As used herein, the term "classical machine learning classifier" refers to a machine-learning based classifier that requires feature selection and/or feature engineering for inputs to the classifier. In contrast, a deep learning neural network is an example of a machine-learning based classifier that does not require feature engineering or feature selection. As explained in more detail below, the classical machine learning classifier 700 may be configured to predict a probability for each image being classified as a portion or a segment of the GIT. The classical machine learning classifier 700 may include, for example, a linear logistic regression classifier and/or a support vector machine (SVM). In various embodiments, the classical machine learning classifier 700 does not include a CNN or other deep learning network.

The linear logistic regression classifier is a classical machine learning classifier. The linear logistic regression classifier estimates the parameters of a logistic model which best describes the probabilities of each sample to belong to each one of the classes. The linear logistic regression classifier is a supervised learning model. Logistic regression is estimating the parameters of a logistic model. The support vector machine is a supervised learning model with associated learning algorithms that analyze data used for classification. In various embodiments, the output of the support vector machine may be normalized between "0" and "1."

In some methods in accordance with this disclosure, inputs to the classical machine learning classifier 700 may include one or more of the classification scores 702 of the deep learning neural network 500 (see FIG. 5), and/or additional cues 704.

The estimated time percentage that the capsule endoscopy device was within the consecutive segments of the GIT or a GIT portion of interest up to a time that the CE device captured the image may be determined, for example, by subtracting the time the CE device captured the first image in the current segment of the GIT (e.g., the descending colon) or the first image in the GIT portion of interest, from time CE device captured a specific image, divided by the total time spent inside the entire GIT portion of interest. The total time spent inside the current segment of the GIT may be calculated by subtracting the time CE device captured the first image in the current segment from time CE captured the last image in the current segment.

In some methods in accordance with this disclosure, the various inputs to the classical machine learning classifier 700 may be used to refine the classification score for one or more of the consecutive segments of the GIT. For example, a SoftMax configured to map the non-normalized output of a network (e.g., the logits of the deep learning neural network) to a probability distribution over predicted output classes, of one or more of the classification scores (e.g., the classification score of the deep learning neural network) may be used as an input to the classical machine learning classifier 700. A SoftMax is a function that takes as input a vector of N real numbers and normalizes it into a probability distribution consisting of N probabilities proportional to the exponentials of the input numbers. That is, prior to applying SoftMax, some vector components could be negative, or greater than one, and might not sum to 1. However, after applying SoftMax, each component will be in the interval (0,1), and the components will add up to 1, so that they can be interpreted as probabilities. For example, a SoftMax of the class 2 score of −0.36 may be 0.36.

The classical machine learning classifier 700 may be trained in a supervised fashion. Images of portions of the GIT may be labeled and used as training data. Persons skilled in the art will understand training the classical machine learning classifier 700 and how to implement it.

In some methods in accordance with this disclosure, the classical machine learning classifier 700 may be used to provide, for images captured by the CE imaging device 212 (see FIG. 2), a classification probability for each segment of the GIT. The classification probability for the images may include each image having a classification probability for a consecutive segment of the GIT. For example, the image classification probabilities may be labeled as a portion of the colon (e.g., cecum, ascending colon, transverse colon, descending colon, and/or rectum).

In some methods in accordance with this disclosure, the classical machine learning classifier 700 may refine the classification probabilities for the plurality of consecutive segments by the classical machine learning classifier 500, and then classify the image to one of the plurality of consecutive segments of the GIT based on the refined classification probabilities from the classical machine learning classifier. For example, an image of a portion of the colon may have classification probabilities such as: class 0 (e.g., cecum): 0; class 1 (e.g., ascending colon): 0; class 2 (e.g., transverse colon): 0.55; class 3 (e.g., descending colon): 0.40; class 4 (e.g., rectum): 0.05. The classical machine learning classifier 700 may refine the classification scores as class 2: 0.9 and classify the image as the transverse colon.

Figure 8:
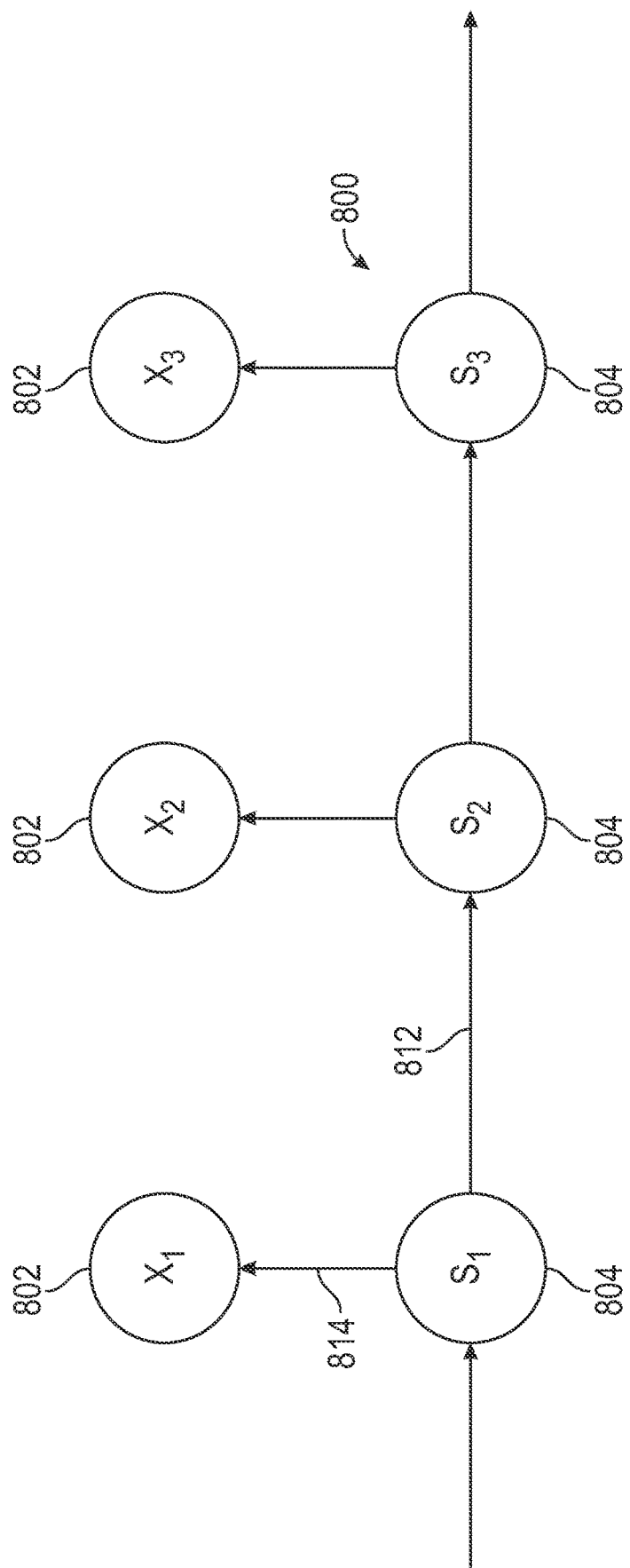
FIG. 8 is a diagram of a Hidden Markov Model in accordance with aspects of the disclosure.

Referring to FIG. 8, a Hidden Markov Model (HMM) 800 is shown in accordance with some aspects of the disclosure. The HMM 800 is a statistical model in which the system being modeled is assumed to be a Markov process (e.g., a sequence of possible events in which the probability of each event depends only on the state attained in the previous event) with unobservable states 804 (e.g., hidden states). The HMM 800 generally consists of observations 802 and a Markov chain of unobservable states 804. According to some aspects, an HMI model may be employed to classify and/or segment a stream of images. Different techniques and adaptations which may be used to apply HMM models to classify and/or segment a stream of images, and specifically, to segment a stream of in-vivo images of the GIT captured via CE, are detailed herein below.

For example, S may be a state 804 and may represent a segment of the GIT (e.g., the cecum). X may be an output 802 of the classical machine learning classifier 700. The transition probability 812 is the probability of transitioning between states 804 (e.g., segments). In some methods, the number of states 804 may be a multiple of the number of consecutive segments of the GIT. For example, if there are five colon segments, there may be fifty states, ten for each colon segment. This may allow entering more information to the HMI 800. For example, a transition to the next segment may not be allowed only after one image. In another example, sometimes, the cecum may not be imaged, and the ascending colon is only imaged at the beginning. In this case, one may enter state 1 of the ascending colon and not state 2 of the ascending colon. Furthermore, ICV would be in state 1 of the ascending colon, since the ICV is at the beginning of the colon.

In various embodiments, the transition probability 812 includes a high probability for staying at the same state 804 and a low probability for changing states 804. Transition can only happen between adjacent states 804. For example, it is not possible to transition between the ascending colon to the descending colon. In some methods, the transition probability 812 includes a zero probability for transitions of more than one segment. Transition backward may have a much lower probability than a transition forward. The emission probability 814 is the probability of having a specific observation in a specific state 804.

In some methods, the transition may happen only between adjacent segments, (e.g., it is impossible to transition between ascending colon 410 straight to descending colon 422, see FIG. 4).

In some methods in accordance with this disclosure, a confusion matrix may be used to refine emission probabilities of the HMM. The confusion matrix is a table that may be used to describe the performance of the model. The table includes an X-axis and a Y-axis. The X-axis may consist of the predicted classes, and the Y-axis may consist of the actual classes. Persons skilled in the art will understand a confusion matrix and how to calculate it.

Figure 9:
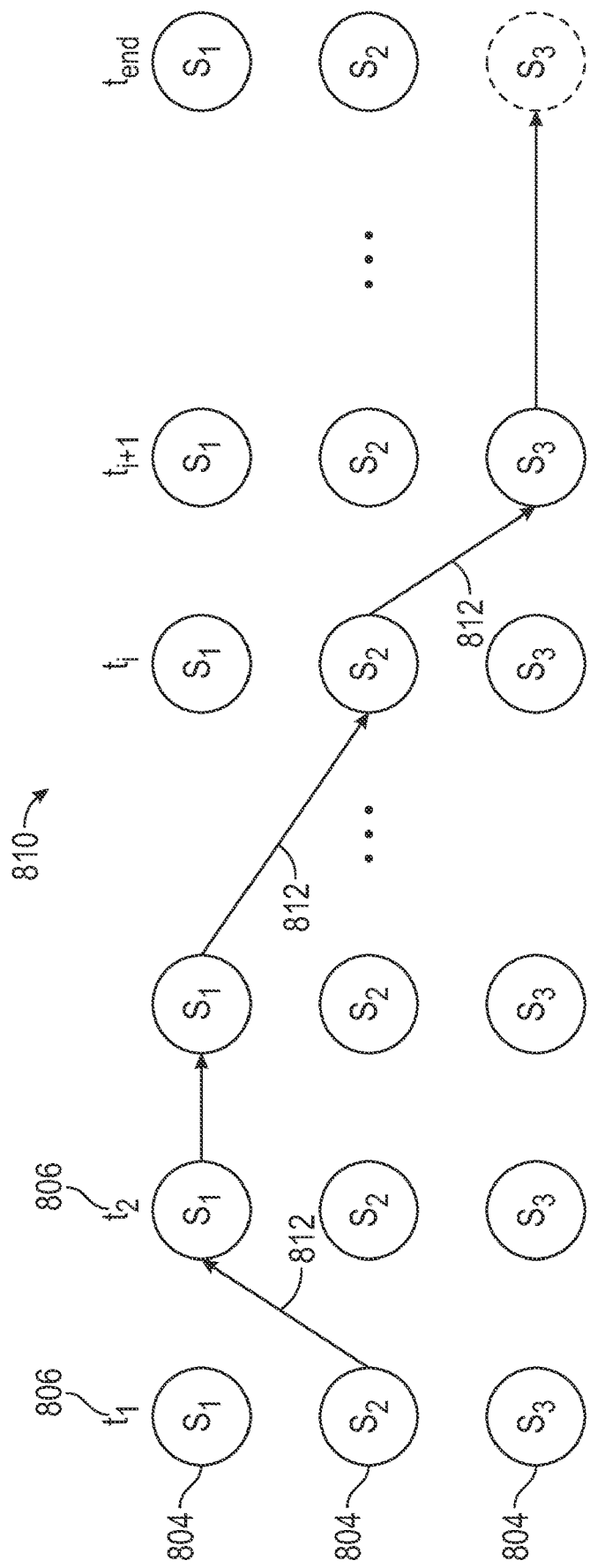
FIG. 9 is a diagram of a Viterbi decoder in accordance with aspects of the disclosure.

Referring to FIG. 9, a generalized block diagram of Viterbi decoding based on the HMM 800 (see FIG. 8) of transitions between consecutive unobservable states 804 (e.g., segments of the GIT 100 or colon 400) is shown in accordance with some aspects of the disclosure. A Viterbi decoder is a deciding algorithm that finds the most probable path between states under HMM model that would best fit the observations. The Viterbi decoder may be used to find the most probable path between states under the HMI 800 model over time that would best match the outputs of the classical machine learning classifier 700. For example, the Viterbi decoding may be used to determine the most probable path between a plurality of consecutive segments of the GIT based on the HMM 800 model and the outputs of the classical machine learning classifier 700. Each t 806 is an image (e.g., frame), each S is a state 804 of the HMI 800 (i.e., a segment of the GIT). Each t 806 includes a classification provided by the classical machine learning classifier 700 to classify the image to a segment of the GIT.

For example, if the CE imaging device 212 (FIG. 2) captures 9000 images in the colon 400 (FIG. 4), then t=1 to 9000. The task of the Viterbi decoding for each frame t 806 is to determine a state 804 of the HMM 800 (i.e., segment of the GIT) that the frame t 806 belongs in. The Viterbi decoding performs this for all frames.

Figure 10:
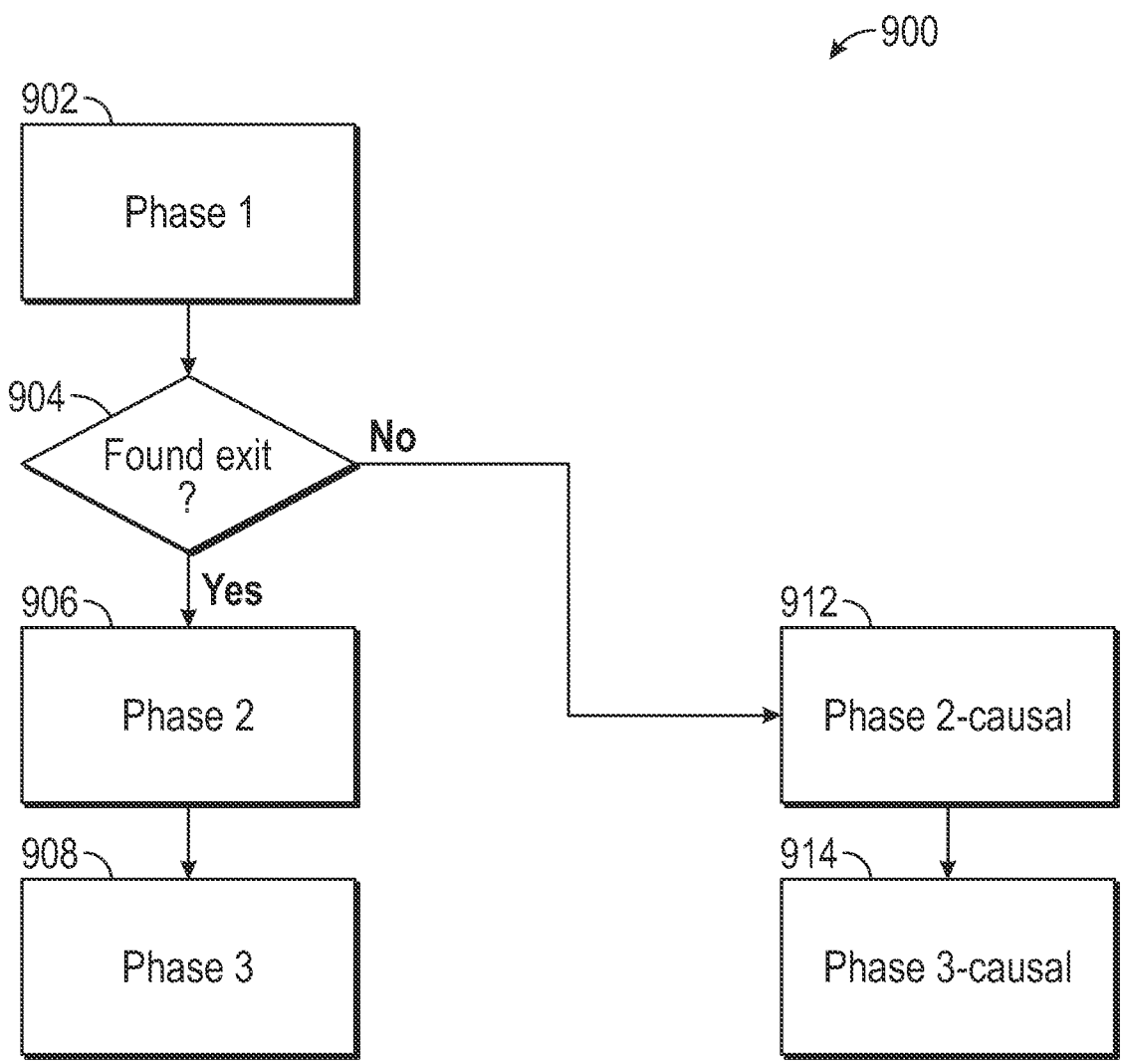
FIG. 10 is a flowchart of a method for classifying images in accordance with aspects of the disclosure.

The flow diagram of FIG. 10 shows a computer implemented method 900 for segmenting or classifying images, e.g., according to the segments of the GIT detailed above. Persons skilled in the art will appreciate that one or more operations of the method 900 may be performed in a different order, repeated, and/or omitted without departing from the scope of the disclosure. In some methods in accordance with this disclosure, some or all of the operations in the illustrated method 900 can operate using a capsule endoscopy, e.g., device 212 (see FIG. 2), the receiving device 214 (see FIG. 2), and/or the computing system 300 (see FIG. 2). Other variations are contemplated to be within the scope of the disclosure. The operations of FIG. 10 will be described with respect to a computing device, e.g., computing system 300 of system 200 (FIG. 2) for analyzing medical images captured in vivo via a CE procedure, or any other suitable computing system device or location thereof including a remotely-disposed computing device. It will be understood that the illustrated operations are applicable to other systems and components thereof as well. The colon may be used as an example, and the disclosed methods may apply to segmentation of any stream of images, including images of any portion of the GIT.

A system 200 for analyzing medical images captured in vivo via a CE procedure, includes a capsule system 210 configured to capture images of the GIT and a computing system 300 configured to process the captured images. The capsule system 210 may include a swallowable CE imaging device 212 (e.g., a capsule) configured to capture images of the GIT as the CE imaging device 212 travels through the GIT. The images may be stored on the CE imaging device 212 and/or transmitted to a receiving device 214, typically including an antenna. The receiving device 214 receives and may store (e.g., within a storage device in the receiving device) the images. The CE imaging device 212 may include one or more cameras or imaging devices, power source(s), processor(s), and transmitter(s).

Initially, at step 902, phase one of the method, the computing system 300 (e.g., a cloud-based system) accesses a plurality of images (e.g., a time series of images) of at least a portion of a GIT (e.g., the colon 400) captured by a CE device. The computing system 300 provides a classification score for each of a plurality of consecutive segments of the GIT by one or more deep learning neural network(s) 500 (see FIG. 5) (or any suitable machine learning algorithm). For example, the computing system 300 may receive as input an image of a portion of the colon and provide (e.g., five) classification scores such as: class 0 (e.g., cecum): 0.920; class 1 (e.g., ascending colon): 0.08; class 2 (e.g., transverse colon): 0; class 3 (e.g., descending colon): 0; class 4 (e.g., rectum): 0. According to some aspects, computing system 300 may further determine or calculate the classification scores for each image.

Next, at step 904, the computing system 300 may receive an indication of whether one of the images includes an exit or not, from an exit detection algorithm (which generally may be composed of one or more algorithms) that checks if there is exit from the GIT portion of interest (i.e., if the capsule captured images of the entire e.g., colon or the entire portion of the GIT to be imaged). The exit detection algorithm may include a transition detector, such as, for example, a binary classification network (e.g., a classic machine learning algorithm or a deep learning algorithm). For example, for the colon it may provide a binary classification such as body, or out of body. In some cases, for example, a SoftMax function may be used to transform the classification scores to probabilities. The signal may be then analyzed in time to identify candidates for transition and select the transition point. The exit detection algorithm may include using a classification score resulting from, for example, an "out of body" classification score from the classification scores from step 902. Based on whether or not an exit is indicated, either a causal or a non-causal model may be used by the classical machine learning classifier 700. For a causal model, for example, the computing system 300 may make a determination using only the images and classifications of the images prior to the current image. For a non-causal model, the computing system 300 may use information relating to images after the current image. In various embodiments, the determination of an exit in one of the images indicates that the non-causal model should be used. For example, the computing system 300 determines that the image includes an exit. According to some aspects, computing system 300 may further determine whether one of the images includes an exit or not. According to some aspects, step 904 is optional. In case step 904 is not applied, then steps 912 and 914 may be performed instead of steps 906 and 908, as detailed below.

If an exit is received ("Yes" at step 904, non-casual case), then at step 906, phase two of the method, the computing system 300 refines the classification score for one or more of the plurality of consecutive segments of the GIT by a classical machine learning classifier 700, based on the non-causal model, and provides a classification probability for each segment of the plurality of consecutive segments of the GIT based on the refined classification scores from the classical machine learning classifier. In the non-casual case, the classical machine learning classifier 700 may receive as input additional features which require the traversing of the entire GIT portion to be imaged by the capsule or the completion of the procedure (e.g., by identifying "exit"). Such features may include time percent and/or progress percent. Time percent is the estimated time percentage that the capsule endoscopy device was within the GIT portion of interest and up to a time that the capsule endoscopy device captured the image. It may be calculated based on the time of capture of the images. Progress percent is an estimation of the percent of the displacement done by the capsule up until each image and relative to the whole GIT portion to be imaged. A displacement of the capsule per image may be calculated based on a motion score determined for each image. The motion score indicates a state of movement\static for the particular image/frame. The motion score may be calculated, for example, by using a classical machine learning classifier and a set of relevant features including features relating to the surrounding frames/images. For example, based on the exit being received, the classical machine learning classifier 700 may receive as inputs the classifications of the deep learning neural network(s) 500 and the time percent in the colon.

Finally, at step 908 (phase three), the computing system 300 determines the classification for each image to one segment of the plurality of consecutive segments of the GIT portion of interest (e.g., colon) based on the refined classification probabilities (from step 906), by processing a signal (e.g., error correction) corresponding to the classifications of the plurality of images over time. For example, the method may determine the classification for the image as the cecum based on the revised classification probability.

In some methods in accordance with this disclosure, the processing of the signal may include MAPP decoding or Viterbi decoding based on an HMM of transitions between the consecutive segments of the GIT (FIGS. 8 and 9). In some methods, the HMM may include a predetermined number of states that is a multiple of a number of the consecutive segments of the GIT. For example, if the colon is divided into five segments, and the multiple is ten, then the predetermined number of states may be fifty states.

In some methods, when revising the classification scores, the computing system 300 processes the signal based on the detection of any relevant anatomical landmark and revises the classification score, e.g., by a predefined vector. For example, if the portion of the GIT is the colon, then the ileocecal valve (ICV) detection score may be used in revising the classification score. For example, computing system 300 may access the score of ICV detection for the image and revise the classification probabilities from the classical machine learning classifier 700. The output of the classical machine learning classifier 700 may be replaced by a fixed probabilities vector for each ICV frame (i.e., a frame determined as displaying the ICV based on the ICV detection score).

In some methods, the transition may happen only between adjacent segments, (e.g., it is impossible to transition between ascending colon 410 straight to descending colon 422, see FIG. 4).

In some methods, if an exit is not found at step 904 then a casual model of the classical machine learning classifier 700 should be used at step 912. Next, at step 912 (phase two—casual), the computing system 300 refines the classification score for at least one of the plurality of consecutive segments of the GIT by a classical machine learning classifier 700, based on some causal inputs, e.g., inputs which do not require information about following or subsequent images, or inputs which do not require the imaging of the entire portion of interest. Such inputs may be the identification of an anatomical landmark (e.g., ICV) or the output of a transition algorithm which identified a transition between two anatomical portions (e.g., identification of a transition from the small bowel to the colon).

Finally, at step 914 (phase three—casual), the computing system 300 determines the classification for each image to one segment of the plurality of consecutive segments of the GIT based on the refined classification probabilities (from step 912), by processing a signal (e.g., error correction) corresponding to the classifications of the plurality of images over time. In some methods, the revised classifications of the images may be displayed on a display. For example, the classification for an image may be the ascending colon 410 and be revised by step 914 to the cecum 404, based on the revised classification probability.

In general, steps 912 and 914 correspond to steps 906 and 908, mutatis mutandis. For example, in the casual case or according to the casual method, features which require the imaging of the entire portion of interest may not be used.

According to some aspects, the casual method (i.e., including steps 902, 912 and 914) may be used to perform an online classification and/or segmentation of a stream of images or a set of images which was already captured and received by a processing system. Such as system 300. The online classification and/or segmentation is performed during the procedure and before the CE device, for example, has exited the body.

In some methods in accordance with this disclosure, the processing of the signal may include MAPP decoding or Viterbi decoding based on an HMM of transitions between the consecutive segments of the GIT. In some methods, the HMM may include a predetermined number of states that is a multiple of a number of the consecutive segments of the GIT. For example, if the colon is divided into five segments, and the multiple is ten, then the predetermined number of states may be fifty states. In some methods, computing system 300 may access a score of ileocecal valve (ICV) detection for the image and revise the classification probabilities from the classical machine learning classifier 700. The output of the classical machine learning classifier 700 may be replaced by a fixed probabilities vector for each ICV frame. When revising the classification scores, the computing system 300 processes the signal based on the ICV detection score.

According to some aspects, images captured via a CE procedure may be segmented according to the disclosed systems and methods, and then may be displayed in a localized manner, e.g., by indicating which image is located in which segment, for example, displaying an image along with location information indicating the location where the image was captured within the GI tract. According to some aspects, the generation of a study of a CE procedure may include segmentation of images of the study according to the disclosed systems and methods. The study may then include image localization information, e.g., in which segment each image is located. In CE, the anatomical location of a pathology identified in an image, for example, may assist or affect the diagnosis and may affect or determine the treatment provided to the patient. The segmentation may also allow a separate characterization for each segment of the GIT portion of interest and may allow a reader of a study to evaluate each segment separately. The segmentation may provide more information to the reader, which may be used to diagnose, evaluate the clinical situation of the patient, and/or recommend treatment. For example, in some cases, one segment may be of more interest than the others, or in some cases, different segments may have different influences on the study evaluation performed by the reader/reviewer or may be considered in a different manner. For example, in some embodiments, once the captured images are segmented, e.g., into anatomical segments, a cleansing score may be evaluated and assigned to each segment. Although the cleansing level of some segments of the GIT portion of interest may be low, a "good" score in a segment of interest may still allow the reader to extract reliable information and/or conclusions from the study. The display of the images may include an indication in which segment each image is located.

Figure 11:
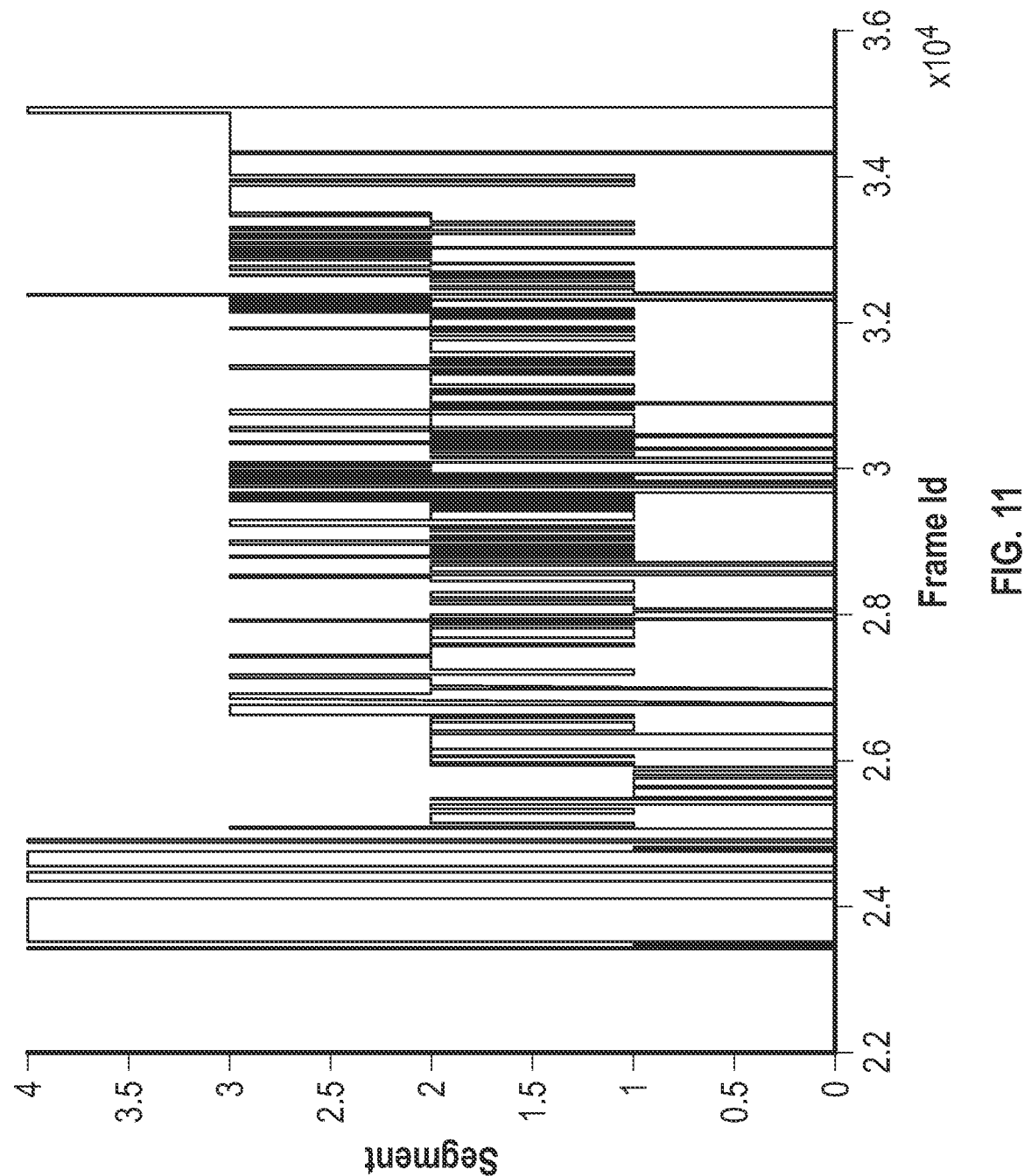

With reference to FIGS. 11 and 12, signals corresponding to the classifications of the plurality of images over time after the various steps of method 900 are shown. For example, a signal corresponding to the classifications of the plurality of images over time based on the one or more deep learning neural network(s) 500, when graphed, may look like FIG. 11. By refining the classification scores for each of the images, the signal corresponding to the classifications of the plurality of images over time, for example, may look like trace 1202 of FIG. 12. Finally, after step 908, the signal corresponding to the classifications of the plurality of images over time may look like trace 1204 of FIG. 12.

Even though the examples are shown and described with respect to images captured in vivo by a CE device, the disclosed technology can be applied to images captured by other devices, mechanisms or procedures, including colonoscopy and enteroscopy procedures and anatomical images captured by Mill, for example.

The embodiments disclosed herein are examples of the disclosure and may be embodied in various forms. For instance, although certain embodiments herein are described as separate embodiments, each of the embodiments herein may be combined with one or more of the other embodiments herein. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

The phrases "in an embodiment," "in embodiments," "in various embodiments," "in some embodiments," or "in other embodiments" may each refer to one or more of the same or different embodiments in accordance with the present disclosure. A phrase in the form "A or B" means "(A), (B), or (A and B)." A phrase in the form "at least one of A, B, or C" means "(A); (B); (C); (A and B); (A and C); (B and C); or (A, B, and C)."

Any of the herein described operations, methods, programs, algorithms, or codes may be converted to, or expressed in, a programming language or computer program embodied on a computer or machine readable medium. The terms "programming language" and "computer program," as used herein, each include any language used to specify instructions to a computer, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, Python, scripting languages, Visual Basic, metalanguages which themselves specify programs, and all first, second, third, fourth, fifth, or further generation computer languages. Also included are database and other data schemas, and any other metalanguages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

It should be understood that the foregoing description is only illustrative of the present disclosure. To the extent consistent, any or all of the aspects detailed herein may be used in conjunction with any or all of the other aspects detailed herein. Various alternatives and modifications can be devised by those skilled in the art without departing from the disclosure. Accordingly, the present disclosure is intended to embrace all such alternatives, modifications, and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A system for image classification, the system comprising:
    at least one processor; and
    at least one memory including instructions stored thereon which, when executed by the at least one processor, cause the system to:
        access a plurality of images of at least a portion of a gastrointestinal tract (GIT) captured by a capsule endoscopy device;
        for each image of the plurality of images:
            provide a classification score for each segment of a plurality of consecutive segments of the GIT by at least one deep learning neural network, and
            provide a classification probability for each segment of the plurality of consecutive segments of the GIT based on the classification scores by a classical machine learning classifier; and
        determine a classification for each image to one segment of the plurality of consecutive segments of the GIT based on processing a signal corresponding to the classification probabilities of the plurality of images.

2. The system of claim 1, wherein in providing the classification probability, the instructions, when executed by the at least one processor, cause the system to, for each image of the plurality of images:
    access a score of an anatomical landmark detection for the image; and
    provide the classification probability based on the score of the anatomical landmark detection.

3. The system of claim 1, wherein the instructions, when executed by the at least one processor, further cause the system to display, on a display, an indication of a location of the image corresponding to a segment of the GIT based on the determined classification.

4. The system of claim 1, wherein the classical machine learning classifier includes a linear logistic regression classifier.

5. The system of claim 1, wherein the instructions, when executed by the at least one processor, further cause the system to receive an indication that at least one image of the plurality of images includes an exit image.

6. The system of claim 5, wherein in providing the classification probability, the instructions, when executed by the at least one processor, cause the system to, for each image of the plurality of images:
    in a case where the indication is received, include as input to the classical machine learning classifier, at least one cue which is based on the indication of the exit image.

7. The system of claim 6, wherein the at least one cue includes at least one of: a time percentage indicating a time that the capsule endoscopy device captured the image over a time duration that the capsule endoscopy device was within a GIT portion of interest, or a progress percent indicating a displacement of the capsule up until each image and relative to a whole GIT portion to be imaged.

8. The system of claim 1, wherein processing the signal includes at least one of a MAPP decoding or a Viterbi decoding based on a Hidden Markov Model of transitions between the consecutive segments of the GIT.

9. The system of claim 8, wherein the Hidden Markov Model includes a predetermined number of states that is a multiple of a number of the consecutive segments of the GIT.

10. The system of claim 1, wherein in processing the signal, the instructions, when executed by the at least one processor, further cause the system to:
    apply a non-zero initial state probability for at least one segment of the plurality of consecutive segments of the GIT; and
    apply a zero initial state probability for at least one other segment of the plurality of consecutive segments.

11. A method for image classification, the method comprising:
    accessing a plurality of images of at least a portion of a gastrointestinal tract (GIT) captured by a capsule endoscopy device;
    for each image of the plurality of images:
        providing a classification score for each segment of a plurality of consecutive segments of the GIT by at least one deep learning neural network,
        provide a classification probability for each segment of the plurality of consecutive segments of the GIT based on the classification scores by a classical machine learning classifier; and
    determining a classification for each image of the plurality of images to one segment of the plurality of consecutive segments of the GIT based on processing a signal corresponding to the classification probabilities of the plurality of images.

12. The method of claim 11, wherein providing the classification probability includes, for each image of the plurality of images:
    accessing a score of an anatomical landmark detection for the image; and
    provide the classification probability based on the score of the anatomical landmark detection.

13. The method of claim 12, wherein the anatomical landmark is an ileocecal valve.

14. The method of claim 11, further comprising displaying, on a display, an indication of a location of the image corresponding to a segment of the GIT based on the determined classification.

15. The method of claim 11, wherein the classical machine learning classifier includes at least one of a linear logistic regression classifier.

16. The method of claim 11, further comprising receiving an indication that at least one image of the plurality of images includes an exit image.

17. The method of claim 16, wherein providing the classification probability includes, for each image of the plurality of images:
    in a case where the indication is received, including as input to the classical machine learning classifier at least one cue which is based on the indication of the exit image.

18. The method of claim 11, wherein processing the signal includes at least one of a MAPP decoding or a Viterbi decoding based on a Hidden Markov Model of transitions between the consecutive segments of the GIT.

19. The method of claim 11, wherein the at least the portion of the GIT is the colon.

20. A system for image classification, the system comprising:
- at least one processor; and
- at least one memory including instructions stored thereon which, when executed by the at least one processor, cause the system to:
  - access a time series of images of at least a portion of a gastrointestinal tract (GIT) captured by a capsule endoscopy device;
  - for each image of the time series of images, classify the image to one segment of a plurality of consecutive segments of the GIT based on classification scores provided by at least one deep learning neural network; and
  - perform error correction to revise the classification of at least one image of the images of the time series of images.

21. The system of claim 20, wherein performing error correction to revise at least one of the classifications, the instructions, when executed by the at least one processor, causes the system to display, on a display, an indication of a location of the image corresponding to a segment of the GIT based on the revised classification.

22. The system of claim 20, wherein performing error correction includes at least one of a MAPP decoding or a Viterbi decoding based on a Hidden Markov Model of transitions between the consecutive segments of the GIT.

* * * * *